United States Patent [19]

Olsen

[11] 4,422,455
[45] Dec. 27, 1983

[54] RESTRAINING DEVICE

[75] Inventor: Alan J. Olsen, Cordova, Tenn.

[73] Assignee: Danek Medical, Inc., Cordova, Tenn.

[21] Appl. No.: 289,971

[22] Filed: Aug. 4, 1981

[51] Int. Cl.³ .............................................. A61F 13/00
[52] U.S. Cl. .................................. 128/134; 128/157; 128/DIG. 15
[58] Field of Search ............... 128/133, 134, 157, 165, 128/166, 171, DIG. 15; 24/72; 2/319, 321; 54/68; 119/96

[56] References Cited

U.S. PATENT DOCUMENTS

| | | | |
|---|---|---|---|
| 1,596,792 | 8/1926 | Barry et al. | 128/134 |
| 2,706,477 | 4/1955 | Daake | 128/134 |
| 3,535,718 | 10/1970 | Murcott | 128/133 |
| 3,536,068 | 10/1970 | Stubbs | 128/134 |
| 3,878,844 | 4/1973 | Tobias | 128/134 |
| 3,939,829 | 2/1976 | Spann | 128/133 |
| 3,947,927 | 4/1976 | Rosenthal | 128/DIG. 15 |
| 4,027,666 | 6/1977 | Marx | 128/DIG. 15 |

Primary Examiner—Henry J. Recla
Assistant Examiner—Karin M. Reichle
Attorney, Agent, or Firm—Walker & McKenzie

[57] ABSTRACT

A device for restraining a patient, i.e., the device usually would be used in pairs with one such device being used to restrain one arm of the patient while another such device would be used to restrain his other arm. Although, the device may also be used in like fashion for restraining either of the legs, if desired. The device generally comprises four main parts, namely: a cuff part for bindable placement about either arm or leg; an anchoring part for attachment to structure of the patient's bed, wheelchair, etc.; an elongated strap for extending the reach between the cuff part and the anchoring part, thus the anchoring part will be inaccessible to the patient; and quick release structure for effectively facilitating expeditious release of the patient when desired and for subseqently returning him to the original restraint condition with minimum effort. The quick release part preferably is situated adjacent the anchoring part so it too will be inaccessible to the patient.

14 Claims, 9 Drawing Figures

RESTRAINING DEVICE

BACKGROUND OF THE INVENTION

1. Field of the Invention

This invention relates to the field of devices used for restraining a patient and is particularly directed toward the type of restraining device which incorporates provisions for facilitating expeditious release of the patient if and when such need arises.

2. Description of the Prior Art

Heretofore, the typical restraining device incorporating structure for enabling rapid release of the patient from the restraining device was dependent upon a key and lock apparatus which required the medical practitioner to carry a key for releasing the patient. Often times, urgency dictated that the patient be released immediately and the necessary key, for some reason or another, was not available. This impediment necessitated that the medical practitioner resort to drastic measures in releasing the patient, i.e., severing the restraining device with scissors or the like, thus rendering the device unserviceable for future use.

Other restraining devices have been developed which incorporate a simple clasp fastener of the type usually found on inexpensive dog leashes and the like, see for example, a U.S. Pat. No. 3,536,068 issued to Stubbs in 1970. Certain of these prior restraining devices incorporate structure which acts like a noose on the wrist, i.e., the structure engaging the wrist tightens about the wrist as the patient applies a pulling force which, of course, results in reducing circulation or perhaps completely cutting off the circulation. Often times, the patient will be under the influence of medication and not realize what he is doing, thus the restraining device renders harm to the patient. The above mentioned Stubbs patent is an example of the noose type restraining device.

In addition, previous restraining devices were intended to simply be attached to the side rails of the bed, i.e., the bars that are often times used to prevent a patient from rolling out of bed. Thus, this arrangement, being in line with the upper surface of the mattress, permits the patient to have access to the restraint which often enables him to eventually be successful in releasing his restraint.

Other U.S. patents pertaining to similar devices as known by the applicant include the following: U.S. Pat. No. 3,297,026 granted to Van Pelt in 1967 and U.S. Pat. No. 3,939,829 granted to Spann in 1976. It should be noted that none of the above mentioned patents suggests or discloses applicant's device.

Therefore, it would appear that a need exists for a restraining device that may quickly be released (by the medical practitioners) without being severed when emergency conditions exist or to permit the patient to attend to normal biological functions when appropriate.

SUMMARY OF THE INVENTION

The present invention is directed toward overcoming the disadvantages and problems relative to previous restraining devices. The device of the present invention usually would be used in pairs with one such device being used to restrain one arm while another such device would be used to restrain the other arm. Although, the device may also be used in like fashion for restraining each of the legs, if desired. The present device generally comprises four main parts, namely: a cuff part for bindable placement about either arm or leg; an anchoring part for attachment to structure of the patient's bed, wheelchair, etc.; an elongated strap for extending the reach between the cuff part and the anchoring part, thus rendering the anchoring part inaccessible to the patient; and a quick release structure for effectively facilitating expeditious release of the patient, when desired, and for subsequently returning him to the original restraint condition with minimum effort. The quick release part preferably is situated adjacent the anchoring part so it too will be inaccessible to the patient.

The main object of the present invention is to provide a definite convenience for the medical practitioner, i.e., the device can readily be released and subsequently refastened with little or no effort and the use of a lock and key structure is avoided. In addition, the patient may adequately be restrained in such a manner that he does not hurt himself if he attempts to pull on the restraining device, i.e., this is in contrast to certain prior devices wherein a pulling action by the patient resulted in an adverse noose or tightening about the wrist of the patient. Further, the device is virtually tamper proof since the patient does not have access to the quick release apparatus nor to the other structure utilized in properly anchoring the device. Moreover, the device herein disclosed is constructed in such a manner that the anchorable part which is adapted to be fastened to the bed or wheelchair can be totally out of reach, indeed, it can be located underneath the bed or attached to any frame member available.

Furthermore, the device includes structure for precluding the likelihood of the cuff restraining portion from becoming disassociated with the padding, in which event bruises and contusions would be likely, i.e., if the unpadded portion were to come in contact with the skin without the cushioning of the padding which is possible with certain prior devices.

The device of the present invention also includes first adjustable bindable structure for facilitating an initial stabilizing condition of the cuff means about the wrist of the patient and second adjustable bindable structure for subsequently facilitating optimum constraint of the cuff structure about the wrist of the patient.

DESCRIPTION OF THE DRAWINGS

FIG. 1 is a perspective view of the device of the present invention shown with one end thereof suitably engaging the wrist of a patient while the other end thereof is shown suitably attached to rigid structure which may represent the bed, wheelchair or the like.

DESCRIPTION OF THE PREFERRED EMBODIMENT

The device 11 of the present invention is intended for restraining a patient, i.e., the device 11 usually would be used in pairs with one such device 11 being used to restrain one arm (characterized by the letter A) of the patient while another such device 11 would be used to restrain his other arm. Although, the device 11 may also be used in like fashion for restraining either of the legs, as desired. Therefore, it will be appreciated that since the device 11 is intended to be used in pairs which are individually identical one with the other, a disclosure of merely one device 11 will suffice for purposes of this specification.

Figure 2:
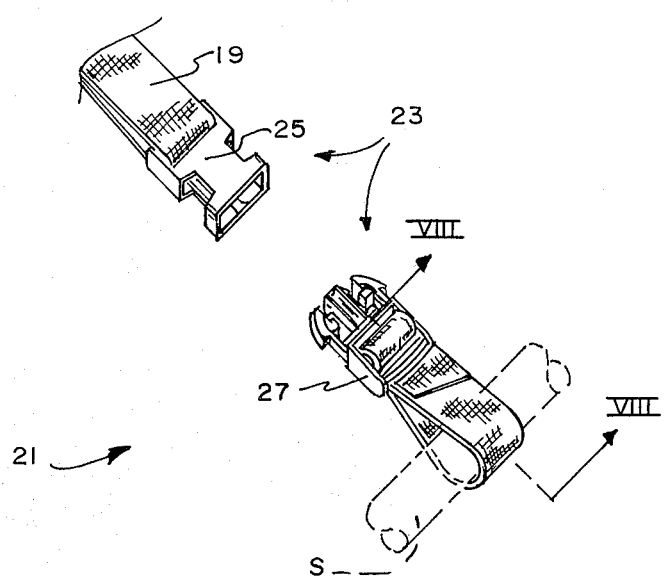
FIG. 2 is a perspective view of merely the anchorable means and quick release means, the latter being shown in a disconnected condition.
Figure 3:
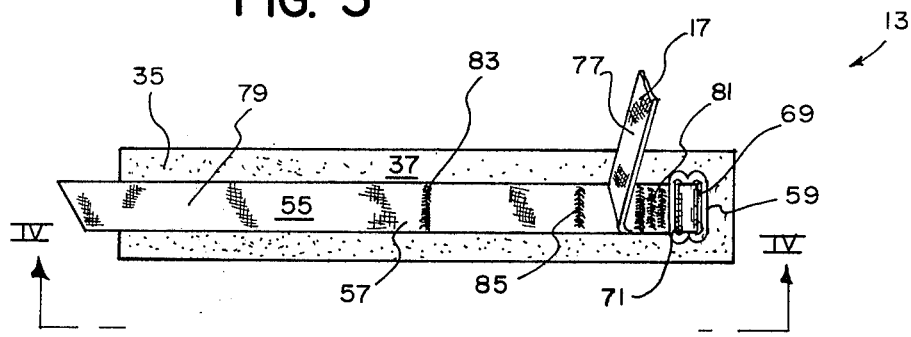
FIG. 3 is a top plan view showing merely the cuff means of the present invention or the structure shown engaging the wrist of the patient in FIG. 1.
Figure 4:
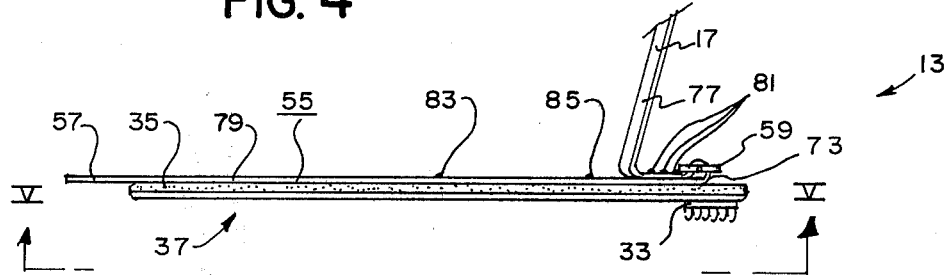
FIG. 4 is a side elevational view of the structure shown in FIG. 3 with the view being taken along the line IV—IV thereof.

The device 11 generally comprises adjustable cuff means, as at 13, for bindable placement about an extremity (either the arm A or leg) of the patient. Also included is elongated strap means, as at 15, having a proximal end, as at 17, affixed to the cuff means 13 and a distal end, as at 19, remotely situated therefrom. Included therewith will also be anchorable means, as at 21, for fixable attachment of the device 11 to certain rigid structure, as at S, which may be inaccessible to the patient, i.e., the inaccessible structure S may be any suitable framing of the wheelchair or the bed which preferably will be well out of reach of the patient. The device 11 also includes quick release means, generally indicated at 23, which includes separable cooperating receptacle and clasp members which respectively are characterized by the numerals 25, 27 in FIG. 2 of the drawings. One of the cooperating members, e.g., the receptacle member 25, is affixed to the distal end 19 of the elongated strap means 15 in a manner as best viewed in FIG. 7; while the other cooperating member, e.g., the clasp member 27, is affixed to the anchorable means 21 in a manner as best viewed in FIG. 8. The function of the quick release means 23 is to provide a means for effectively facilitating expeditious release of the patient, when desired, and for subsequently returning him to the original restraint condition with minimum effort.

A particular buckle or quick release device which fully meets the requirements of the present invention for the quick release means 23 and which includes separable cooperating receptacle and clasp members is shown in U.S. Pat. No. 4,150,464 granted Apr. 24, 1979 to Richard J. Tracy. This patent has been assigned to the Illinois Tool Works, Inc., Chicago, Ill. and is presently being marketed by Fastex a division of the Illinois Tool Works, Inc. and which is situated at 195 Olgonquin Road, Des Plaines, Ill. 60016. Therefore, merely a brief description of this buckle will suffice for present purposes. Accordingly, reference should be made to the Tracy patent for a more detailed description of the character and structure of the quick release means 23 or buckle as patented by Richard J. Tracy.

Indeed, it would only be fair to give due credit to the Tracy patent for the immense contribution it makes in the effectiveness of the present invention. However, it should be mentioned that no specific purposes were mentioned in the Tracy disclosure. Therefore, the Tracy patent does not suggest or disclose any of the features of the present invention, i.e., other than the explicit details of the quick release means 23 or buckle.

The adjustable cuff means alluded to above includes first adjustable bindable means, as at 29, for facilitating an initial stabilizing condition of the cuff means 13 about the arm A of the patient. The specific structure of the first adjustable bindable means 29 will be disclosed later in the specification.

The adjustable cuff means also includes second adjustable bindable means, as at 31, for subsequently facilitating optimum constraint of the cuff means 13 about the arm A of the patient. Here again, the specific structure of the second adjustable bindable means 31 will be disclosed later in the specification.

It should be noted that the first and second adjustable bindable means 29, 31 enable the device 11 to be substantially universally adaptable to the different sizes of patients. Therefore, one such device 11 constructed in accordance with the present invention is intended to be adaptable to most patients.

Particular attention will now be directed toward FIGS. 3–6 of the drawings wherein it may be seen that the first adjustable bindable means 29 preferably includes a separable fastening device, as at 32, comprising cooperable elements, as at 33, 35, respectively formed from sections of hook and pile fabric. More specifically, the cooperable elements 33, 35 are constructed somewhat in accordance with a U.S. Pat. No. 3,083,737 granted to George deMestral on Apr. 2, 1963 and which was assigned to International Velcro Company, Estab., Nyon, Switzerland, a corporation of Liechtenstein. Therefore, a brief disclosure of the cooperable elements 33, 35 will suffice for the present invention. Accordingly, reference should be made to the deMestral patent for a more detailed description of the character and structure of these cooperable elements 33, 35. It should be mentioned that hook and pile fabric has, over the years, been used extensiveley in many industries and is usually referred to as Velcro fasteners.

The adjustable cuff means 13 preferably includes an elongated web of padding, as at 37, which is of sufficient length for adequately overlappingly girdling the arm A of the patient with the separable fastening device 32 being fixedly attached thereto, in a manner to be described, wherein one of the cooperable elements, e.g., the pile fabric element 35, defines at least a portion of the outer surface of the padding 37 and the cooperable element other than said element 35, e.g., the hook fabric element 33, defining at least a portion of the inner surface of the padding 37. In this manner, the mere face to face pressing engagement of the cooperable elements 33, 35 (which is achieved in part as the padding 37 overlappingly engages the arm of the patient) is effective in hooking or engaging the cooperative elements 33, 35. Accordingly, it will be appreciated by those skilled in the art that ease of separation of the cooperable elements 33, 35 requires a peeling apart force of considerable magnitude, in this way an initial stabilizing condition of the cuff means 13 about the arm A of the patient is established. In this manner, the separable fastening device 32 greatly facilitates applying the device 11 by holding the cuff means in place about the arm A while the second bindable means 31 may be brought into play. The elongated web of padding 37 preferably is formed, at least in part, by a well-known polyurethane open pore foam having suitable thickness, e.g., $\frac{3}{8}$ of an inch or 9.5 millimeter or the like, to protect the arm A of the patient from bruises or contusions while the patient is constrained with the device 11. In addition, the polyurethane open pore foam preferably is laminated to strong pile fabric which defines at least a portion of the outer surface of the elongated web of padding 37, in this manner, the laminated pile fabric establishes the pile fabric cooperable element 35.

Figure 1:
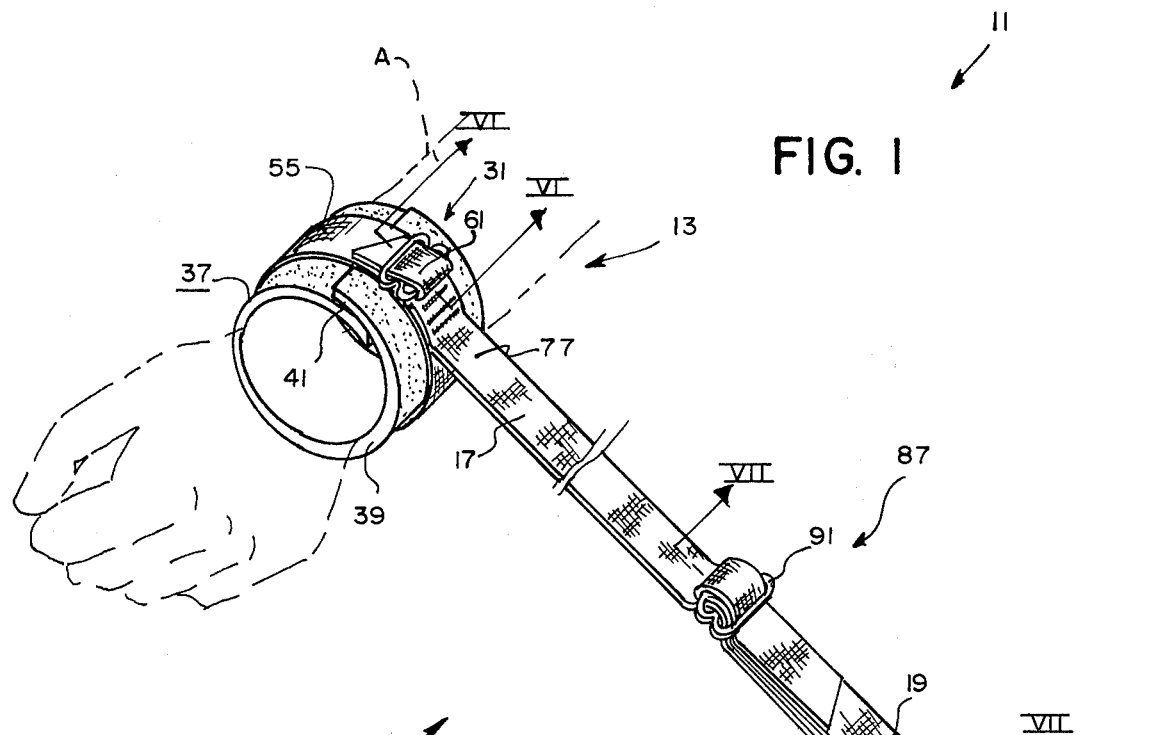

Moreover, the elongated web of padding 37 preferably includes a single girth portion, as best illustrated in FIG. 1 by the numeral 39, which is intended for being placed in contiguous engagement with the arm A. The pile fabric 35 defines substantially the entire outer surface of the single girth portion 39. In addition, the elongated web of padding 37 includes an overlapping portion, as best shown in FIG. 1 of the drawings by the numeral 41, which is intended to overlappingly engage the single girth portion 39. Furthermore, the cooperable element or hook fabric 33 is fixedly attached to the inner surface of the overlapping portion 41, whereby overlapping engagement of the overlapping portion 41 any where along the single girth portion 39 is effective in bringing into operation the separable fastening device 32.

Figure 5:
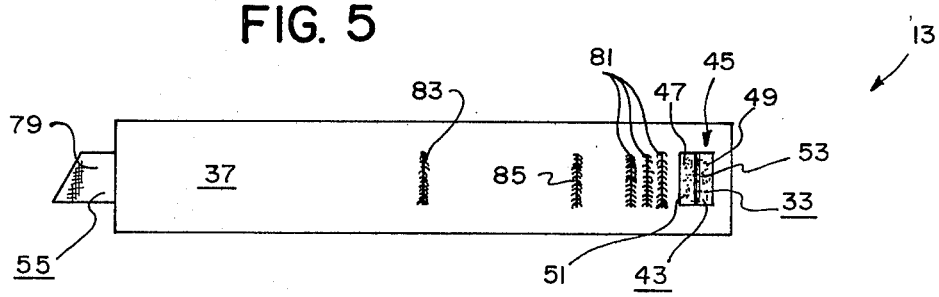
FIG. 5 is a bottom plan view of the structure shown in FIG. 4 with the view being taken along the line V—V thereof.
Figure 9:
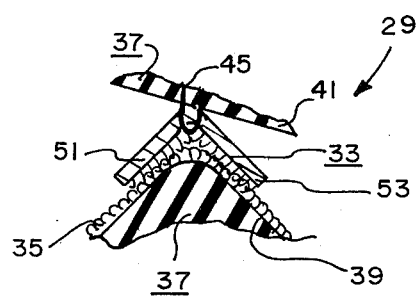
FIG. 9 is a partial sectional view of the structure circumscribed by the circular line IX of FIG. 6 with the view intended to depict certain structure in a displaced configuration from that shown in FIG. 6.

More specifically, the cooperable element or hook fabric 33 consists of an oblong section of flexible hook fabric as best shown in FIG. 5 of the drawings by the numeral 43, wherein the length thereof is substantially 180–200% of the width and the longitudinal axis thereof is perpendicularly disposed with respect to the longitudinal axis of the elongated web of padding 37. In addition, the oblong section of flexible hook fabric 43 is fixedly attached to the elongated web of padding 37 by a hinge seam, as at 45 in FIGS. 5, 6 and 9 of the drawings, thus constituting hinge means, i.e., either the hinge seam or the hinge means may be characterized by the numeral 45, for enhancing the effectiveness of the first adjustable bindable means 29, in a manner about to be disclosed. It may clearly be seen that the hinge means 45 extends substantially parallel with the longitudinal axis of the oblong section of flexible hook fabric 43 and is disposed substantially midway between the longitudinal marginal portions thereof, i.e., the longitudinal marginal portions being characterized by the numerals 47, 49. In this manner, a pair of freely foldable wing sections, as at 51, 53 are established by the oblong section of flexible hook fabric 43, thus the wing sections 51, 53 are free to swing about the hinge means 45. It will be appreciated by those skilled in the art that the pair of foldable wing sections 51, 53 enhance the holding ability of the separable fastening device 32 by inherently assuming a somewhat folded condition, i.e., as clearly indicated in FIG. 9 of the drawings, when a normal pulling force is applied to the overlapping portion 41, thus resisting the peeling action necessary in properly separating the cooperable elements 33, 35 one from the other.

From FIG. 1 of the drawings it may readily be seen that the second adjustable bindable means 31 includes elongated band means, as at 55, which has a portion thereof fixedly attached to the outer surface of the elongated web of padding 37, in a manner to be described, for circumferentially engaging the arm A of the patient, while the elongated web of padding 37 is protectively sandwiched between the arm A and the elongated band 55.

Particular attention will now be directed toward FIGS. 3–6 of the drawings wherein it may be seen that the elongated band means 55 alluded to above includes an elongated flexible band member, as at 57, and a first buckle, as at 59, which is compatibly sized for engagement with the flexible band member 57 is a specific fashion, to be described as this specification proceeds. The band means 55 also includes primary lock means, as at 61, for locking the elongated flexible band member 57 to the first buckle 59. In this manner, the possibility of inadvertent loosening of the second adjustable bindable means 31 is precluded, and the patient is denied the opportunity of removing himself from the device 11.

More specifically, the primary lock means 61 alluded to above includes constructing the first buckle 59 from a rigid substance, e.g., steel or the like, so as to have three parallel spaced apart rib members, as at 63, 65, 67, which jointly define first and second elongated slots, as at 69, 71 respectively. From FIG. 3 of the drawings it may readily be seen that the lengths of the slots 69, 71 are compatibly sized with respect to the width of the elongated flexible band member 57.

Figure 6:
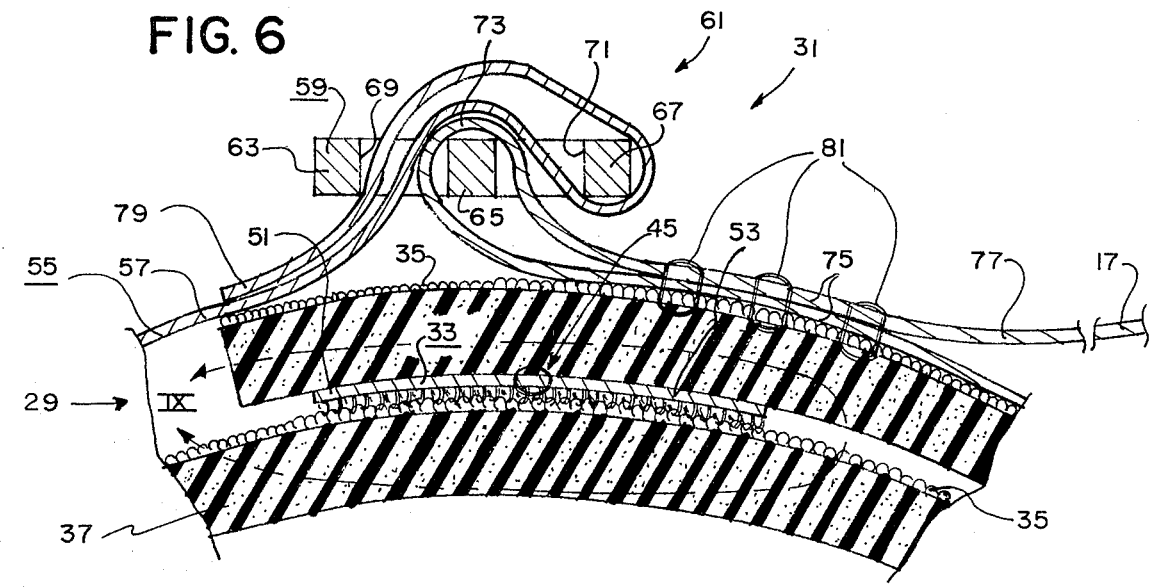
FIG. 6 is an enlarged sectional view taken as on the line VI—VI of FIG. 1.

Moreover, from FIG. 6 of the drawings it may be seen that the elongated flexible band member 57 may be threadedly received in the first and second slots 69, 71 wherewith a medial portion, as at 73, of the band member 57 embraces the rib member 65 (which is clearly the intermediate one of the ribs). From FIGS. 3–6 of the drawings, it may be seen that in this manner the band member 57 establishes a proximal double thickness portion, as at 75 in FIG. 6, and first and second somewhat free distal portions, as at 77, 79, i.e., the first distal portion 77 is integrally joined to the proximal end 17 of the elongated strap means 15 as clearly shown in FIGS. 1 and 3–6 of the drawings.

Furthermore, the adjustable cuff means 13 includes primary seam means, as at 81, for joining the proximal double thickness portion 75 to the elongated web of padding 37. Further yet, the widths of the first and second elongated slots 69, 71 are constructed so as to have predetermined dimensions which are commensurate with the thickness of the elongated flexible band member 57. The widths of the slots 69, 71 (being somewhat critical) merely enable the second free distal portion 79 to be passed first (upwardly as viewed in FIg. 6 or) in a forwardly direction through the first slot 69, thence in a forwardly direction (or downwardly) through the second slot 71, and to subsequently be doubled back around one of the outer ribs, i.e., the rib 67, so as to ultimately be snuggingly passed (downwardly or) in a rearward direction again through the first slot 69. In this manner, the elongated flexible band member 57 is effectively locked to the first buckle 59 by the primary lock means 61.

The adjustable cuff means 13 also includes secondary seam means, as at 83, for medianly joning the elongated band means 55 and the elongated web of padding 37 one with the other. The adjustable cuff means 13 also includes tertiary seam means, as at 85, which is medially disposed between the primary and secondary seam means 81, 83 for aiding in joining the elongated band means 55 and the elongated web of padding 37 one with the other.

Figure 7:
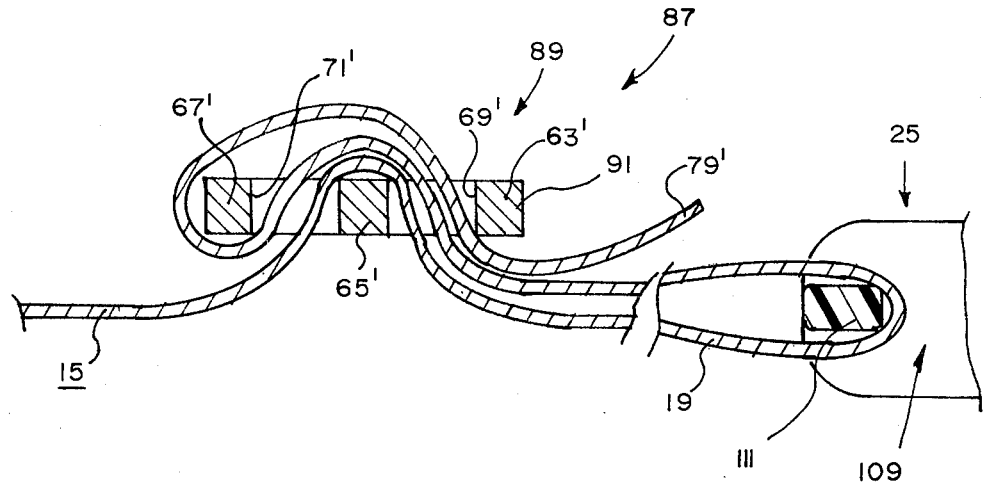
FIG. 7 is an enlarged partial sectional view taken as on the line VII—VII of FIG. 1.

Referring now to FIGS. 1 and 7 of the drawings wherein it may be seen that the elongated strap means 15 includes length adjustable means, as at 87, for facilitating the act of making an adjustment to the length of the strap means 15. Moreover, the elongated strap means 15 includes secondary lock means, as at 89, for locking the length adjustable means 87 in any of its various positions, thus precluding inadvertent loosening thereof and also denying the patient the opportunity of removing himself from the device 11.

The length adjustable means 87 includes a second buckle, as at 91, which is substantially a duplicate of the first buckle 59. Moreover, the secondary lock means 89 alluded to above is substantially identical to the primary lock means 61. Therefore, in the interest of convenience and brevity, the verbage necessary to describe the secondary lock means 89 will be omitted.

Since the secondary lock means 89 is substantially identical to the primary lock means 61, the structure pertaining the the secondary lock means, i.e., as shown in FIG. 7 of the drawings will be distinguishable from that shown in FIG. 6 of the drawings by adding a prime suffix, e.g., the three rib members will be designated at 63′, 65′, and 67′, etc.

Figure 8:
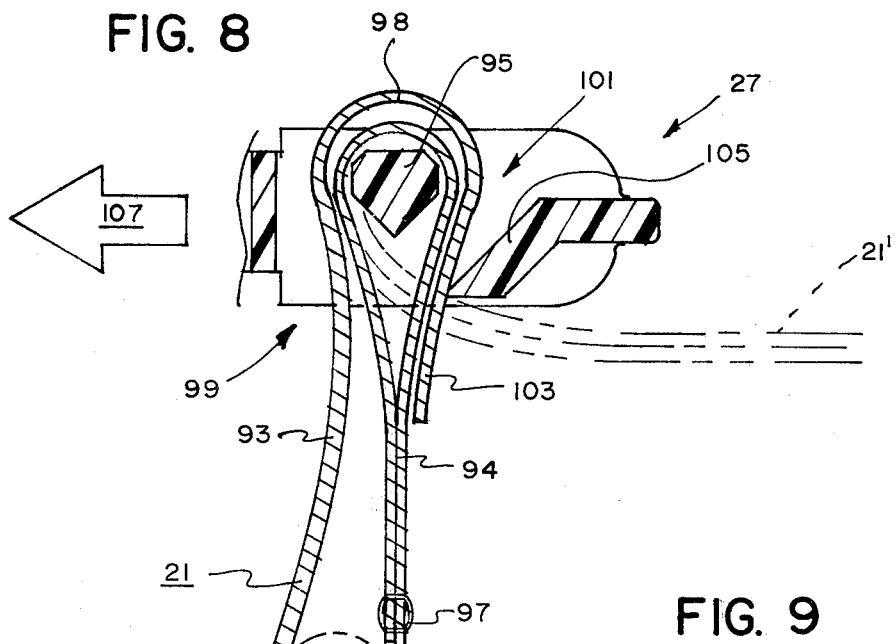
FIG. 8 is an enlarged sectional view taken substantially as on the line VIII—VIII of FIG. 2, however, certain structure has been rotated substantially 90° in a clockwise direction.

A portion of the clasp member 27 is shown in FIG. 8 of the drawings along with the anchorable means 21. Moreover, a preferred arrangement for attaching the anchorable means 21 with the clasp member 27 is clearly shown in FIg. 8 of the drawings. Accordingly, the anchorable means 21 includes a belt member 93 having one end, as at 94, circumposed about a rib 95 and attached therewith in any well-known manner, as with a seam 97, thus establishing a free end, as at 98. The belt member 93 preferably is intended to be manually circumposed about the support structure S and is subsequently threadedly received upwardly through a slot, as at 99, of the clasp member 27. The belt member 93 is then threadedly received downwardly through a second slot, as at 101, of the clasp member 27, so that a terminous end thereof, as at 103, extends at least a short distance beyond a belt gripping rib, as at 105, which is also part of the clasp member 27. Accordingly, as the patient applies pulling force in the direction of an arrow, as at 197, the anchorable means 21 assumes a position as shown in broken lines and characterized in FIG. 8 of the drawings by the numeral 21′. In this manner, the belt gripping rib 105 grips the terminous end 103 of the belt member 93 in such a manner that any slippage of the anchorable means 21 is precluded, i.e., since the gripping action increases directly proportional to the pulling force.

It should be understood that the receptacle member 25 includes a slot, as at 109 in FIG. 7 of the drawings, through which the elongated strap means 15 may freely extend. In addition, the receptacle member 25 also includes a rib, as at 111, about which the distal end 19 of the strap means 15 may be circumposed, as clearly shown in FIG. 7 of the drawings.

Although the invention has been described and illustrated with respect to a preferred embodiment thereof, it should be understood that it is not intended to be so limited since changes and modifications may be made therein which are within the full intended scope of the invention.

I claim:

1. A device for restraining a patient to a certain rigid structure, said device comprising adjustable cuff means for bindable placement about an extremity of the patient, elongated strap means having a proximal end affixed to said cuff means and a distal end remotely situated therefrom, anchorable means for fixable attachment to said distal end of said strap means and to said certain rigid structure which may be inaccessible to the patient, and quick release means including separable cooperating receptacle and clasp members—one of which being affixed to said distal end of said elongated strap means with the other of said members being affixed to said anchorable means—for effectively facilitating expeditious release of said anchorable means from said distal end of said strap means to allow release of the patient when desired and for subsequently returning him to the original restraint condition with minimum effort, said proximal end of said strap means being affixed to said cuff means, said adjustable cuff means includes first adjustable bindable means for facilitating an initial stabilizing condition of said cuff means about the extremity of the patient and second adjustable bindable means operable in conjunction with said first adjustable bindable means for subsequently facilitating optimum constraint of said cuff means about the extremity of the patient whereby said cuff means is prevented from tightening about the patient's extremity in the event the patient attempts to pull said distal end of said strap means from said anchorable means.

2. The device as set forth in claim 1 in which said first adjustable bindable means includes a separable fastening device comprising cooperable elements respectively formed from sections of hook and pile fabric.

3. The device as set forth in claim 2 in which said adjustable cuff means includes an elongated web of padding for overlappingly girdling the extremity of the patient with said separable fastening device being fixedly attached thereto wherein one of said cooperable elements defines at least a portion of the outer surface of said elongated web of padding and the cooperable element other than one of said cooperable elements defining at least a portion of the inner surface of said elongated web of padding, thus the mere face to face pressing engagement of said cooperable elements (as the padding overlapping engages the extremity of the patient) is effective in hooking the cooperative elements together whereby separation requires a peeling apart force of considerable magnitude, in this way an initial stabilizing condition of said cuff means about the extremity of the patient is established.

4. The device as set forth in claim 3 in which said elongated web of padding is formed at least in part by polyurethane open pore foam to protect the extremity of the patient from bruises and contusions while being constrained with said device, and said polyurethane open pore foam being laminated to strong pile fabric which defines at least a portion of the outer surface of said elongated web of padding thus establishing one of said cooperable elements.

5. The device as set forth in claim 4 in which said elongated web of padding includes a single girth portion intended for being placed in contiguous engagement with the extremity, said pile fabric defining substantially the entire outer surface of said single girth portion, and in which said elongated web of padding includes an overlapping portion intended to overlappingly engage the single girth portion, and in which said cooperative element other than said one of said cooperable elements is fixedly attached to the inner surface of said overlapping portion, werey overlapping engagement of said overlapping portion anywhere along said single girth portion is effective in bringing into operation said separable fastening device.

6. The device as set forth in claim 1 in which said adjustable cuff means includes an elongated web of padding to protect the extremity of the patient from bruises and contusions while being constrained with said device, and in which said second adjustable bindable means includes elongated band means having a portion thereof fixedly attached to the outer surface of said elongated web of padding for circumferentially engaging the extremity of the patient while said elongated web of padding is protectively sandwiched between the extremity and said elongated band means.

7. The device as set forth in claim 6 in which said elongated band means includes an elongated flexible band member and a first buckle compatibly sized for engagement with said flexible band member, and primary lock means for locking said elongated flexible band member to said first buckle, thus precluding inadvertent loosening of said second adjustable bindable means and also denying the patient the opportunity of removing himself from said device.

8. A device for restraining a patient to certain rigid structure which may be inaccessible to the patient, said device comprising adjustable cuff means for bindable placement about an extremity of the patient, elongated strap means having a proximal end affixed to said cuff means and a distal end remotely situated therefrom, anchorable means for fixable attachment to said distal end of said strap means and to said certain rigid structure, and quick release means including separable cooperating receptacle and clasp members—one of which being affixed to said distal end of said elongated strap means with the other of said members being affixed to said anchorable means—for effectively facilitating expeditious release of said anchorable means from said distal end of said strap means to allow release of the patient when desired and for subsequently returning to him the original restraint condition with minimum effort; said adjustable cuff means including first adjustable bindable means for facilitating an initial stabilizing condition of said cuff means about the extremity of the patient, said first adjustable bindable means including a separable fastening device comprising cooperable elements respectively formed from sections of hook and pile fabric; said adjustable cuff means including an elongated web of padding for overlapping girdling the extremity of the patient with said separable fastening device being fixedly attached thereto wherein one of said cooperable elements defines at least a portion of the outer surface of said elongated web of padding and the cooperable element other than one of said cooperable elements defining at least a portion of the inner surface of said elongated web of padding, thus the mere face to face pressing engagement of said cooperable elements (as the padding overlappingly engages the extremity of the patient) is effective in hooking the cooperative elements together whereby separation requires a peeling apart force of considerable magnitude, in this way an initial stabilizing condition of said cuff means about the extremity of the patient is established; said elongated web of padding being formed at least in part by polyurethane open pore foam to protect the extremity of the patient from bruises and contusions while being constrained with said device, said polyurethane open pore foam being laminated to strong pile fabric which defines at least a portion of the outer surface of said elongated web of passing thus establishing one of said cooperable elements; said elongated web of padding including a single girth portion intended for being placed in contiguous engagement with the extremity, said pile fabric defining substantially the entire outer surface of said single girth portion, said elongated web of padding including an overlapping portion intended to overlappingly engage the single girth portion; said cooperative element other than said one of said cooperable elements being fixedly attached to the inner surface of said overlapping portion, whereby overlapping engagement of said overlapping portion anywhere along said single girth portion is effective in bringing into operation said separable fastening device, said cooperative element other than said one of said cooperable elements consisting of an oblong section of flexible hook fabric wherein the length thereof is substantially 180-200% of the width and the longitudinal axis thereof is perpendicularly disposed with respect to the longitudinal axis of said elongated web of padding, said oblong section of flexible hook fabric being fixedly attached to said elongated web of padding by a hinge seam thus constituting hinge means for enhancing the effectiveness of said first adjustable bindable means, said hinge means extending substantially parallel with the longitudinal axis of said oblong section of flexible hook fabric and being disposed substantially midway between the longitudinal marginal portions thereof, in this manner a pair of freely foldable wing sections are established by said oblong section of flexible hook fabric with said wing sections being free to swing about said hinge means, said pair of foldable wing sections enhancing the holding ability of said separable fastening device by inherently assuming a somewhat folded condition when a normal pulling force is applied to said overlapping portion thus resisting the peeling action necessary in properly separating said cooperable elements one from the other.

9. A device for restraining a patient to certain rigid structure which may be inaccessible to the patient, said device comprising adjustable cuff means for bindable placement about an extremity of the patient, elongated strap means having a proximal end affixed to said cuff means and a distal end remotely situated therefrom, anchorable means for fixable attachment to said distal end of said strap means and to said certain rigid structure, and quick release means including separable cooperating receptacle and clasp members—one of which being affixed to said distal end of said elongated strap means with the other of said members being affixed to said anchorable means—for effectively facilitating expeditious release of said anchorable means from said distal end of said strap means to allow release of the patient when desired and for subsequently returning him to the original restraint condition with minimum effort; said adjustable cuff means including first adjustable bindable means for facilitating an intital stabilizing condition of said cuff means about the extremity of the patient; said adjustable cuff means including second adjustable bindable means for subsequently facilitating optimum constraint of said cuff means about the extremity of the patient; said adjustable cuff means, including an elongated web of padding to protect the extremity of the patient from bruises and contusions while being constrained with said device, said second adjustable bindable means including elongated band means having a portion thereof fixedly attached to the outer surface of said elongated web of padding for circumferentially engaging the extremity of the patient while said elongated web of padding is protectively sandwiched between the extremity and said elongated band means; said elongated band means including an elongated flexible band member and first buckle compatibly sized for engagement with said flexible band member, and primary lock means for locking said elongated flexible band member to said first buckle, thus precluding inadvertent loosening of said second adjustable bindable means and also denying the patient the opportunity of removing himself from said device; said first buckle being constructed from a rigid substance having three parallel spaced apart rib members jointly defining at least in part first and second elongated slots having the length thereof compatibly sized with respect to the width of said elongated flexible band members, said elongated flexible band member being threadedly received in said first and second slots wherewith a medial portion of said elongated flexible band member embraces the intermediate one of said ribs, thus said elongated flexible band member establishes a proximal double thickness portion and first and second somewhat free distal portions, the first of said distal portions being integrally joined to the proximal end of said elongated strap means, said adjustable cuff means including primary seam means for joining the proximal double thickness portion of said elongated web of padding; the widths of said first and second elongated slots being constructed with predetermined dimensions which are commensurate with the thickness of said elongated flexible band member for merely enabling the second free distal portion thereof to be passed first in a forwardly direction through said first elongated slot, then in a forwardly direction through said second elongated slot, and to subsequently be double back around one of the outer ribs so as to ultimately be snuggingly passed in a rearward direction again through said first elongated slot, thus said elongated flexible band member may effectively be locked to said first buckle by said primary lock means.

10. The device as set forth in claim 9 in which said adjustable cuff means includes secondary seam means for medianly joining said elongated band means and said elongated web of padding one with the other.

11. The device as set forth in claim 10 in which said adjustable cuff means includes tertiary seam means medially disposed between said primary and secondary means for aiding in joining said elongated band means and said elongated web of padding one with the other.

12. The device as set forth in claim 9 in which said elongated strap means includes length adjustable means for facilitating the act of making an adjustment to the length thereof, and in which said elongated strap means includes secondary lock means for locking said length adjustable means in any of its various positions, thus precluding inadvertent loosening thereof and also denying the patient the opportunity of removing himself from said device.

13. The device as set forth in claim 12 in which said length adjustable means includes a second buckle which is substantially a duplicate of said first buckle, and in which said secondary lock means is substantially identical to said primary lock means.

14. A device for restraining a patient to certain rigid structure, said device comprising adjustable cuff means for bindable placement about an extremity of the patient, elongated strap means having a proximal end affixed to said cuff means and a distal end remotely situated therefrom, anchorable means for fixable attachment to said distal end of said strap means and to said certain rigid structure which may be inaccessible to the patient, and quick release means including separable cooperating receptacle and clasp members—one of which being affixed to said distal end of said elongated strap means with the other of said members being affixed to said anchorable means—for effectively facilitating expeditious release of said anchorable means from said distal end of said strap means to allow release of the patient when desired and for subsequently returning him to the original restraint condition with minimum effort; said cuff means including an elongated member for overlappingly girdling the extremity of the patient and including adjustable bindable means for stabilizing said elongated member about the extremity of the patient, said adjustable bindable means including pile fabric fixedly attached to the outer surface of said elongated member and including an oblong section of flexible hook fabric fixedly attached to inner surface of said elongated member with the mere face to face pressing overlapping engagement of said pile and hook fabric being effective in binding said cuff means about the extremity of the patient, the length of said oblong section of flexible hook fabric being substantially 180–200% of the width and the longitudinal axis thereof being perpendicularly disposed with respect to the longitudinal axis of said elongated member, said oblong section of flexible hook fabric being fixedly attached to said elongated member by a hinge seam thus constituting hinge means for enhancing the effectiveness of said adjustable bindable means, said hinge means extending substantially parallel with the longitudinal axis of said oblong section of flexible hook fabric and being disposed substantially midway between the longitudinal marginal portions thereof, in this manner a pair of freely foldable wing sections are established by said oblong section of flexible hook fabric with said wing sections being free to swing about said hinge means, said pair of foldable wing sections enhancing the holding ability of said adjustable bindable means by inherently assuming a somewhat folded condition when a normal pulling force is applied to said overlapping portion thus resisting the peeling action necessary in properly separating said cooperable elements one from the other.

* * * * *